United States Patent
Özarslan

(10) Patent No.: US 11,789,106 B2
(45) Date of Patent: Oct. 17, 2023

(54) MAGNETIC RESONANCE METHOD, SOFTWARE PRODUCT, AND SYSTEM FOR DETERMINING A DIFFUSION PROPAGATOR OR RELATED DIFFUSION PARAMETERS FOR SPIN-LABELLED PARTICLES

(71) Applicant: Evren Özarslan, Linköping (SE)

(72) Inventor: Evren Özarslan, Linköping (SE)

(73) Assignee: KALMIA AB, Linkoping (SE)

( * ) Notice: Subject to any disclaimer, the term of this patent is extended or adjusted under 35 U.S.C. 154(b) by 0 days.

(21) Appl. No.: 17/913,619

(22) PCT Filed: Mar. 26, 2021

(86) PCT No.: PCT/SE2021/050273
§ 371 (c)(1),
(2) Date: Sep. 22, 2022

(87) PCT Pub. No.: WO2021/201753
PCT Pub. Date: Oct. 7, 2021

(65) Prior Publication Data
US 2023/0124954 A1    Apr. 20, 2023

Related U.S. Application Data

(60) Provisional application No. 63/001,266, filed on Mar. 28, 2020.

(51) Int. Cl.
*G01V 3/00* (2006.01)
*G01R 33/563* (2006.01)
(Continued)

(52) U.S. Cl.
CPC ........ *G01R 33/56341* (2013.01); *A61B 5/055* (2013.01); *G01R 33/58* (2013.01)

(58) Field of Classification Search
CPC .............. G01R 33/3415; G01R 33/543; G01R 33/5659; G01R 33/36; A61B 5/055
(Continued)

(56) References Cited

U.S. PATENT DOCUMENTS

| | | | |
|---|---|---|---|
| 2009/0322331 A1* | 12/2009 | Buracas | G01R 33/5614 |
| 2014/0091790 A1* | 4/2014 | Huwer | G01R 33/56341 |
| | | | 324/318 |
| 2018/0049665 A1* | 2/2018 | Jeong | A61B 5/055 |

FOREIGN PATENT DOCUMENTS

| | | | |
|---|---|---|---|
| EP | 3493151 A1 | 6/2019 | |
| WO | WO-2010085796 A2 * | 7/2010 | A61B 5/055 |

(Continued)

OTHER PUBLICATIONS

International Searching Authority, International Search Report and Written Opinion received for International Application No. PCT/SE2021/050273, dated Jun. 17, 2021, 9 pages, Swedish Patent and Registration Office, Sweden.

(Continued)

*Primary Examiner* — Walter L Lindsay, Jr.
*Assistant Examiner* — Frederick Wenderoth
(74) *Attorney, Agent, or Firm* — Alston & Bird LLP

(57) ABSTRACT

The present disclosure relates to a computer implemented diffusion magnetic resonance method for determining a diffusion parameter for spin-labelled particles in a specimen. The method (100) comprises providing (110) a specimen and a magnetic resonance device arranged to measure magnetic resonance in said specimen; applying (120) at least one magnetic field gradient pulse sequence to said specimen, thereby spin-labelling a set of particles comprised in said specimen; obtaining (130) magnetic resonance measurement data corresponding to said at least one magnetic field gradient pulse sequence for said spin-labelled particles with said magnetic resonance device; determining (140) at least (Continued)

one diffusion parameter for said spin-labelled particles based on said obtained measurement data; wherein determining (140) said at least one diffusion parameter comprises forming for each diffusion parameter at least one Fourier transform representing said diffusion parameter based on said obtained measurement data; and wherein each magnetic field gradient pulse sequence comprises at least three gradient pulses wherein at least one gradient pulse is configured to introduce a phase shift in said spin-labelled particles based on their position in said specimen.

13 Claims, 10 Drawing Sheets

(51) Int. Cl.
    *A61B 5/055*      (2006.01)
    *G01R 33/58*      (2006.01)

(58) Field of Classification Search
    USPC .......................................................... 324/309
    See application file for complete search history.

(56) References Cited

FOREIGN PATENT DOCUMENTS

| | | | | |
|---|---|---|---|---|
| WO | WO-2014003643 A1 * | 1/2014 | ........... | A61B 5/0263 |
| WO | WO 2015/158879 A1 | 10/2015 | | |
| WO | WO 2016/132176 A1 | 8/2016 | | |
| WO | WO-2016132176 A1 * | 8/2016 | ............. | A61B 5/031 |
| WO | WO 2018/088954 A1 | 5/2018 | | |

OTHER PUBLICATIONS

Stejskal, E. O., et al., "Spin Diffusion Measurements: Spin Echoes in the Presence of a Time-Dependent Field Gradient", The Journal of Chemical Physics, Jan. 1, 1965, pp. 288-292, vol. 42, No. 1, retrieved from the Internet at <https://www.mriquestions.com/uploads/3/4/5/7/34572113/stejskal_and_tanner1965.pdf> on Sep. 19, 2022, 6 pages.

Viallon, Magalie, et al., "State-of-the-art MRI techniques in neuroradiology: principles, pitfalls, and clinical applications", Neuroradiology, Apr. 10, 2015, retrieved from the Internet at <https://www.academia.edu/20749685/State_of_the_art_MRI_techniques_in_neuroradiology_principles_pitfalls_and_clinical_applications?auto=download> on Sep. 19, 2022, 27 pages.

Yolcu, Cem, et al., "NMR signal for particles diffusing under potentials: From path integrals and numerical methods to a model of diffusion anisotropy", Physical Review E, May 2016, vol. 93, Issue 5, id.052602, retrieved from the Internet at <https://arxiv.org/pdf/1603.06373.pdf> on Sep. 19, 2022, 33 pages.

* cited by examiner

MAGNETIC RESONANCE METHOD, SOFTWARE PRODUCT, AND SYSTEM FOR DETERMINING A DIFFUSION PROPAGATOR OR RELATED DIFFUSION PARAMETERS FOR SPIN-LABELLED PARTICLES

CROSS REFERENCE TO RELATED APPLICATIONS

This application is a National Stage Application, filed under 35 U.S.C. § 371, of International Application No. PCT/SE2021/050273, filed Mar. 26, 2021, which claims priority to U.S. Provisional Application No. 63/001,266, filed Mar. 28, 2020; the contents of both of which as are hereby incorporated by reference in their entireties.

BACKGROUND

Related Field

The present disclosure relates to determining diffusion parameters in a specimen with magnetic resonance techniques.

Description of Related Art

NMR is a well-known technique that has been employed to infer information regarding chemical and structural environments. Magnetic resonance (MR) imaging (MRI) is a method that enables the assignment of different NMR signal values to different positions in space. Localized NMR spectroscopy is a technique where a NMR signal is detected from a particular volume in space.

Using MRI, it is possible to distinguish regions of specimens and biological tissue based on the differences in their MR characteristics leading to "contrast" in MR images. It is also possible to create contrast based on the motion, such as flow and diffusion, of molecules within tissue.

Diffusion magnetic resonance spectroscopy, and magnetic resonance imaging (diffusion MRI) measure the movements of molecules in many materials and biological tissues. Diffusion MRI has been an important technique for assessing the structure of specimens including materials, biological tissue, and porous media.

Diffusion weighted MR measurements can be performed in a controllable way by the introduction of a pair of magnetic field gradient pulses to the common MR pulse sequences. When these diffusion gradients are embedded in a spin-echo based method, the technique is called pulsed gradient spin echo (PGSE) (See E. O. Stejskal, and J. E. Tanner, J. Chem. Phys., 42, 288, (1965)). More generally, the diffusion gradients are employed in pulse sequences including spin-echo based ones and others that detect stimulated echoes and free induction decays.

BRIEF SUMMARY

One object of the invention is improved determination of diffusion parameters for a specimen with magnetic resonance techniques.

This has in accordance with the present disclosure been achieved by means of a computer implemented diffusion magnetic resonance method for determining a diffusion parameter for spin-labelled particles in a specimen. The method comprises providing a specimen and a magnetic resonance device arranged to measure magnetic resonance in said specimen; applying at least one magnetic field gradient pulse sequence to said specimen, thereby spin-labelling a set of particles comprised in said specimen; obtaining magnetic resonance (MR) measurement data corresponding to said at least one magnetic field gradient pulse sequence for said spin-labelled particles with said magnetic resonance device; determining a at least one diffusion parameter for said spin-labelled particles based on said obtained measurement data.

Determining at least one diffusion parameter comprises forming for each diffusion parameter at least one Fourier transform representing said diffusion parameter based on said obtained measurement data. Each magnetic field gradient pulse sequence comprises at least three gradient pulses wherein at least one gradient pulse is configured to introduce a phase shift in said spin-labelled particles based on their position in said specimen.

This has the advantage of allowing a diffusion parameter such as the true diffusion propagator to be estimated, which contains additional information about diffusion compared to the ensemble average diffusion propagator (EAP) that is typically estimated. This further has the advantage of allowing access to previously undiscovered information about the specimen that can be used to generate data and images from the data and obtain new contrasts based on different mathematical parameters. These new contrast mechanisms should provide additional information about the material or tissue microstructure that can improve the specificity and utility of diffusion MR for characterizing alterations, e.g. due to disease in human patients.

The term diffusion parameter is to be understood as a value, set of values, a mathematical expression or a model describing diffusion in a volume.

In some examples determining the at least one diffusion parameter comprises determining a diffusion propagator, a dispersity index, a local variance, a diffusion-weighted image, a steady-state distribution, a joint density distribution, and/or a set of cumulant tensors for said spin-labelled particles.

In some examples applying at least one magnetic field gradient pulse sequence comprises applying gradient pulses configured to introduce two phase shifts in spin-labelled particles comprised in the specimen, based on the particles' positions at two different times.

In some examples each gradient pulse sequence comprises at least two gradient pulses each with a duration shorter than one fourth of the sum of gradient pulse durations of said gradient pulse sequence, and wherein said at least two gradient pulses are configured to introduce a phase shift in said spin-labelled particles based on their position in said specimen, and/or each gradient pulse sequence has an integral of gradient field strength over time for all gradient pulses that is substantially zero.

This has the advantage of allowing a specimen exposed to a long and weak magnetic field gradient pulse and two short and strong magnetic field gradient pulses, wherein the integral of gradient field strength over time is zero, to provide MR measurement data indicative of diffusion occurring between the two short gradient pulses.

In some examples a plurality of gradient pulse sequences are applied, and each gradient pulse sequence has a different gradient strengths, gradient directions, gradient durations and/or delay times between gradient pulses, and determining the at least one diffusion parameter comprises forming the Fourier transform representing each diffusion parameter based on measurement data corresponding to said plurality of gradient pulse sequences.

This has the advantage of allowing the additional gradient pulse sequence(s) to result in additional corresponding MR measurement data that may be used to improve forming said Fourier transform representing said diffusion parameter.

In some examples the method further comprises calibrating said magnetic resonance device based on the determined at least one diffusion parameter.

This has the advantage of allowing a diffusion parameter, such as the diffusion propagator, determined for a reference specimen compared to reference data corresponding to said reference specimen to be indicative of the performance of the magnetic resonance device, such as providing incorrect gradient timings or strengths.

In some examples obtaining magnetic resonance measurement data comprises performing magnetic resonance spectroscopy, localized magnetic resonance spectroscopy, and/or magnetic resonance imaging with said provided magnetic resonance device.

In some examples determining the at least one diffusion parameter comprises utilizing discrete Fourier transform, fast Fourier transform and/or analytical derivations.

The present disclosure further relates to a computer program product comprising a non-transitory computer-readable storage medium having thereon a computer program comprising program instructions, the computer program being loadable into a processor and configured to cause the processor to perform the method for determining a diffusion parameter for spin-labelled particles.

The present disclosure further relates to a magnetic resonance system for determining a diffusion parameter of spin-labelled particles. The system comprises a magnetic resonance device, and computer. The computer is arranged to control said magnetic resonance device to project at least one sequence of magnetic field gradient pulses and radiofrequency pulses into a specimen with the magnetic resonance device;

collect magnetic resonance measurement data from said specimen at a plurality of different gradient durations, gradient strengths and gradient directions with the magnetic resonance device, and the computer being arranged to reconstruct at least one Fourier transform for each at least one diffusion parameter based on the collected magnetic resonance measurement data; and determine the at least one diffusion parameter based on the corresponding reconstructed at least one Fourier transform, wherein each gradient pulse sequence comprises at least three gradient pulses wherein at least one gradient pulse is configured to introduce a phase shift in spin-labelled particles comprised in the specimen based on position.

In some examples of the system, the computer is arranged to project a gradient pulse sequence configured to introduce two phase shifts in spin-labelled particles comprised in the specimen, based on the particles' positions at two different times.

In some examples of the system, the computer is arranged to calibrate the magnetic resonance device based on diffusion measurements.

In some examples of the system, said magnetic resonance device is arranged to obtain measurement data utilizing magnetic resonance spectroscopy, localized magnetic resonance spectroscopy, and/or magnetic resonance imaging.

DETAILED DESCRIPTION OF VARIOUS EMBODIMENTS

Figure 1:
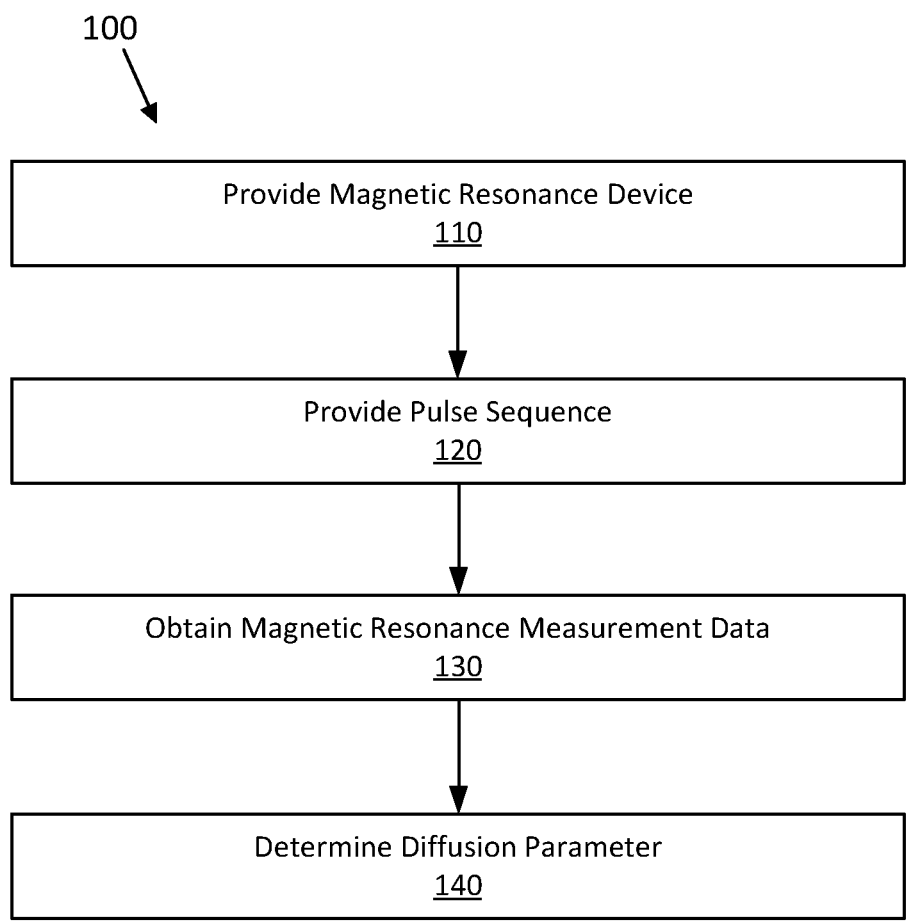
FIG. 1 shows schematically a computer-implemented method for determining a diffusion parameter.

Throughout the figures, same reference numerals refer to same parts, concepts, and/or elements. Consequently, what will be said regarding a reference numeral in one figure applies equally well to the same reference numeral in other figures unless not explicitly stated otherwise.

FIG. 1 shows an example computer implemented diffusion magnetic resonance method for determining a diffusion parameter for spin-labelled particles. The example method 100 comprises providing 110 a specimen and a magnetic resonance device arranged to measure magnetic resonance in said specimen, applying 120 at least one magnetic field gradient pulse sequence to said specimen, thereby spin-labelling a set of particles comprised in said specimen, obtaining 130 magnetic resonance measurement data for said spin-labelled particles corresponding to said applied gradient pulse sequence with said magnetic resonance device, determining 140 at least one diffusion parameter for said spin-labelled particles based on said obtained measurement data, wherein determining 140 said at least one diffusion parameter comprises forming for each diffusion parameter at least one Fourier transform representing said diffusion parameter based on said obtained measurement data, and wherein each gradient pulse sequence comprises at least three gradient pulses wherein at least one gradient pulse is configured to introduce a phase shift in said spin-labelled particles based on their position in said specimen.

In some examples determining 140 at least one diffusion parameter comprises determining a diffusion propagator, a dispersity index, a local variance, a diffusion-weighted image, a steady-state distribution, a joint density distribution, and/or a set of cumulant tensors for said spin-labelled particles.

In some examples of the method 100, wherein applying 120 at least one magnetic field gradient pulse sequence comprises applying gradient pulses configured to introduce two phase shifts in spin-labelled particles comprised in the specimen, based on the particles' positions at two different times. In some examples the method 100 applies 120 a magnetic field gradient pulse sequence configured to introduce at least two phase shifts in spin-labelled particles comprised in the specimen, based on the particles' positions at at least three different times. Typically different times relate to different time intervals, such as a plurality of different time intervals corresponding to a plurality of magnetic field gradient pulses separated in time.

In some examples the method 100 further comprises calibrating the magnetic resonance device based on the determined at least one diffusion parameter. In some of these examples the specimen is a reference specimen with corresponding predetermined diffusion parameter data, such as a container filled with water. A mismatch between the determined diffusion parameter and the corresponding predetermined diffusion parameter data may be indicative a required calibration of gradient timings or gradient strengths.

In some examples the method 100 comprises obtaining a reference specimen and corresponding predetermined diffusion parameter data, and calibrating the magnetic resonance device based on the determined diffusion parameter for said reference specimen and the corresponding obtained predetermined diffusion parameter data.

It is to be understood that applying 120 at least one gradient pulse sequence and obtaining 130 magnetic resonance measurement data are parts of a magnetic resonance measurement of the specimen, and that applying 120 at least one gradient pulse sequence and obtaining 130 magnetic resonance measurement data typically are interdependent and may overlap in time, such as matching radio frequency pulses and magnetic gradient pulses. Comprehensive details on how to perform a magnetic resonance measurement are outside the purview of this description.

In some examples the method comprises performing (not shown) a magnetic resonance measurement of the specimen with the provided magnetic resonance device, wherein performing said magnetic resonance measurement comprises applying 120 at least one gradient pulse sequence and obtaining 130 magnetic resonance measurement data for said spin-labelled particles.

In some examples each gradient pulse sequence comprises at least two gradient pulses configured to introduce a phase shift in said spin-labelled particles based on position.

In some examples of the method, each gradient pulse sequence comprises at least two gradient pulses each with a duration shorter than one fourth of the sum of gradient pulse durations of said gradient pulse sequence. In some of these examples said duration is shorter than one tenth, shorter than one thirtieth, or shorter than one hundredth of the sum of gradient pulse durations of said gradient pulse sequence.

In some of examples a first gradient pulse has a long duration and a low gradient strength, and a second gradient pulse and a third gradient pulse have significantly short durations and higher gradient strength, such that the components of the gradients along any direction integrated over time encompassing all three pulses is substantially zero. This allows the second gradient pulse and the third gradient pulse to phase shift diffusing particles to result in a signal attenuation related to the diffusion propagator and the steady-state distribution of said particles, see Eq.1.

$$E_\Delta(q,q') = \int dx \rho(x) \int dx' P(x', \Delta | x) e^{-i(q \cdot x + q' \cdot x')} \quad \text{(Eq.1)}$$

q and q' are in this example vectors that are determined by, respectively, the second gradient pulse and the third gradient pulses configured to introduce phase shifts that depend on the particles' average positions. $E_\Delta(q,q')$ is the signal attenuation, which is the measured signal divided by the signal when no diffusion gradient is applied. $\Delta$ is in this example the time between the starting times of the second gradient pulse and the third gradient pulse. The diffusion propagator $P(x', \Delta|x)$ represents the probability density that a particle located at position x travels to x' over a time interval of duration $\Delta$. $\rho(x)$ is the steady-state distribution.

When the diffusion process is measured in d dimensions, the diffusion propagator may be obtained based on an estimate of $\rho(x)$ via the 2d-dimensional inverse Fourier transform of the signal attenuation $$P(x', \Delta | x) = \frac{\rho(x)^{-1}}{(2\pi)^{2d}} \int dq\, e^{iq \cdot x} \int dq'\, e^{iq' \cdot x'} E_\Delta(q, q') \quad \text{(Eq. 2)}$$

$\rho(x)$ may be estimated by transforming the subset of the data either with q'=0 or q=0 through the expressions $$\rho(x) = \frac{1}{(2\pi)^d} \int dq\, e^{iq \cdot x} E_\Delta(q, 0) \quad \text{(Eq. 3)}$$

$$\rho(x) = \frac{1}{(2\pi)^d} \int dq'\, e^{iq' \cdot x} E_\Delta(0, q') \quad \text{(Eq. 4)}$$

Thus, the diffusion propagator can be obtained through $$P(x', \Delta | x) = \frac{\int dq\, e^{iq \cdot x} \int dq'\, e^{iq' \cdot x'} E_\Delta(q, q')}{(2\pi)^d \int dq\, e^{iq \cdot x} E_\Delta(q, 0)} \quad \text{(Eq. 5)}$$

In some examples determining 140 said diffusion parameter comprises reconstructing at least one Fourier transform of said diffusion parameter based on said obtained measurement data. In some examples determining 140 said diffusion parameter comprises forming at least one Fourier transform corresponding to said diffusion parameter based on said obtained measurement data. In some examples determining 140 said diffusion parameter comprises forming at least one Fourier transform representing said diffusion parameter based on said obtained measurement data. In some examples determining 140 said diffusion parameter comprises forming at least one Fourier transform related to said diffusion parameter based on said obtained measurement data. In some examples determining 140 said diffusion parameter comprises applying said obtained measurement data to at least one Fourier transform representing said diffusion parameter.

In some examples determining 140 said at least one diffusion parameter comprises forming a mathematical expression representing each diffusion parameter, wherein each mathematical expression comprises at least two Fourier transforms based on said obtained measurement data. In some of these examples at least one of the at least two Fourier transforms comprised in said mathematical expression corresponds to the steady-state distribution, $\rho(x)$. In some examples determining 140 at least one diffusion parameter comprises determining a diffusion propagator by forming a mathematical expression representing said diffusion propagator comprising at least two Fourier transforms based on said obtained measurement data. In some of these examples one of said at least two Fourier transforms comprised in said mathematical expression corresponds to the steady-state distribution, $\rho(x)$.

In some examples applying 120 at least one magnetic field gradient pulse sequence to said specimen comprises applying magnetic field gradients via a set of gradient coils.

In some examples of the method, wherein a plurality of gradient pulse sequences are applied 120, wherein each gradient pulse sequence has a different gradient strengths, gradient directions, gradient durations and/or delay times between gradient pulses.

In some examples of the method forms a mathematical expression representing said diffusion parameter comprising at least one Fourier transforms based on said obtained measurement data, wherein said obtained measurement data corresponds to a plurality of gradient pulse sequences. By utilizing measurement data corresponding to different gradient pulse sequences allows for more accurate Fourier transforms and thus more accurate mathematical expressions representing said diffusion parameter.

In some examples of the method, applying 120 at least one magnetic field gradient pulse sequence comprises applying a pulse sequence configured to obtain the distribution of the average positions of the particles or the associated cumulant tensors.

In some examples obtaining 130 magnetic resonance measurement data comprises performing magnetic resonance spectroscopy, localized magnetic resonance spectroscopy, and/or magnetic resonance imaging with said provided magnetic resonance device.

In some examples determining 140 the at least one diffusion parameter further comprises determining the steady-state distribution of said spin-labelled particles. In some of these examples determining 140 the at least one diffusion parameter comprises determining at least one other diffusion parameter based on said determined steady-state distribution.

In some examples determining 140 the diffusion parameter comprises utilizing analytical derivations, discrete Fourier transform and/or fast Fourier transform.

The provided specimen comprising said spin-labelled particles may be a porous medium, soft-matter, food products, cultured or post mortem biological tissue, simulated materials, simulated tissue, synthetic materials, artificial tissue models, tissue slices and/or cell cultures. In some of these examples the provided specimen is an in vivo and/or ex vivo specimen.

Figure 2A:
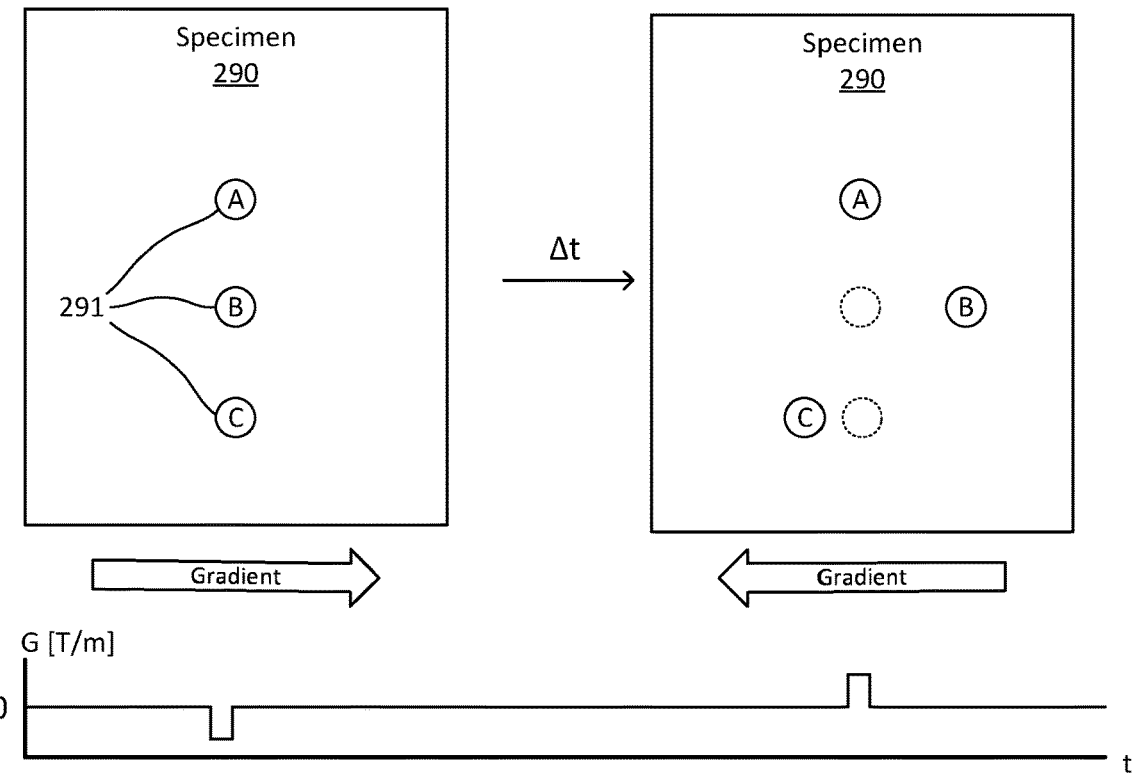
FIG. 2a-b depict schematically a specimen exposed to pulse sequence of magnetic field gradients.
Figure 2B:
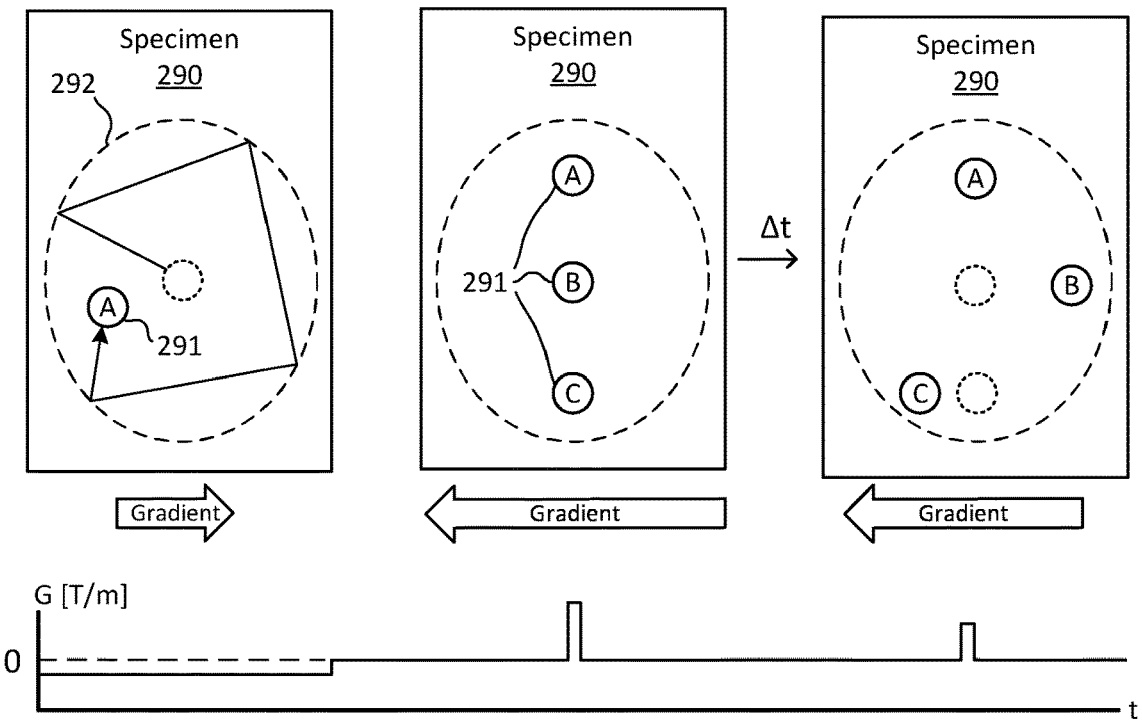

FIG. 2a-b depicts schematically a specimen exposed to pulse sequences of magnetic field gradients. The magnetic field gradient-vs-time plots in the depicted example are for illustrative purposes and may be incorrect in scale.

FIG. 2a depicts schematically a specimen exposed to a pulse sequence comprising two magnetic field gradient pulses. The example depicts a specimen 290 comprising a set of particles 291 during exposure to a first magnetic field gradient pulse and a second magnetic field gradient pulse. The first and the second pulse are represented by gradient arrows and a plot of gradient field strength vs time, indicative of the strength and the directions of the gradient fields.

In the example the set of particles 291 comprised in the specimen 290 are substantially experiencing the same magnetic field strength during the first pulse. After a time $\Delta t$ after the first pulse the set of particles are exposed to magnetic field strengths based on their position by the second pulse. In this example the first and the second pulse have the same durations and gradient strength, and only differ in that the direction of the applied gradient fields are opposite.

In this example the set of particles 291 comprised in the specimen 290 are particles A, B and C. Particle A has, from the pulse sequence, been exposed to magnetic fields of the same strength and duration but with opposite direction. For a correctly configured magnetic resonance measurement using said gradient pulse sequence, particle A and similar unmoving parts may show the same signal a measurement without any applied gradient pulse sequence. Particle B has, from the pulse sequence, been exposed to a stronger magnetic field by the first pulse than the second pulse. Particle C has, from the pulse sequence, been exposed to a stronger magnetic field by the second pulse than the first pulse. In this example the difference in absolute integrated magnetic field strength over time is larger for particle B than particle C, which corresponds to particle B being located further away from the initial position in the direction of the field gradients during the second pulse. For a correctly configured magnetic resonance measurement using said gradient pulse sequence and appropriate corresponding radio frequency pulses the resulting difference in experienced absolute integrated magnetic field strength over time of particle B and particle C may be detected.

It is to be understood that for this example with linear magnetic field gradients across the specimen 290 the set of particles 291 will be exposed to an absolute integrated magnetic field strength over time proportional to the difference in position between the first and second pulse in the direction of the field gradient irrespective of starting position in the specimen 290.

FIG. 2b depicts schematically a specimen 290 exposed to pulse sequence comprising three magnetic field gradient pulses. The example depicts a specimen 290 comprising a set of particles 291 during exposure to a first, a second and a third magnetic field gradient pulses. The first, the second and the third pulses are represented by gradient arrows and a plot of gradient field strength vs time, indicative of the strength and the directions of the gradient fields. In this example, like in the example of FIG. 2a, the integral of gradient field strength over time for the gradient pulse sequence is substantially zero.

In the example in FIG. 2b the set of particles 291 comprised in the specimen 290 are exposed the first pulse, wherein the first pulse is significantly longer duration and significantly lower gradient field strength than the second gradient pulse and the third gradient pulse. During the application of the first pulse, the particles 291 traverse long distances following random trajectories. The effect of the first pulse is to introduce a phase shift proportional to the average positions of the particles 291. Due to the long duration of this pulse, the average for each particle 291 of all trajectories traversed by the particles 291 within the same local environment are typically tightly distributed around the centre of a local structure 292 they are comprised within. Thus, all particles within the same local structure 292 undergo the same phase shift determined by the centre of their local environment within the specimen.

In FIG. 2b the trajectory of particle A 291 is depicted to illustrate how the average position over time may end up close to the centre of its local structure 292 for long durations, thereby resulting in particles 291 experiencing similar average gradient field strengths over the duration.

In this example during the second pulse the set of particles 291 are substantially experiencing the same magnetic field strength during the second pulse. After a time $\Delta t$ after the second pulse the set of particles are exposed to magnetic field strengths based on their position by the third pulse. In this example the second pulse and the third pulse have the same durations and gradient field direction, and only differ in that the gradient field strength is larger for the second pulse than for the third pulse.

In some examples the first, second and third magnetic field gradient pulses each having a different direction. In some examples the pulse sequence comprises at least three magnetic field gradient pulses each having a different direction. In some of these examples the magnetic field gradient over time for the pulse sequence is substantially zero.

As a first parameter example the pulse sequence in FIG. 2b may have durations for the first, the second and the third pulse of 100 ms, 5 ms, and 5 ms respectively; a time between the first and the second pulse of 0.1 ms; and a time between the second and the third pulse of 20 ms. In this example the average gradient field strength of the second and the third pulse being substantially 10 times larger than the gradient field strength of the first pulse would result in the integral of gradient field strength over time for the gradient pulse sequence to be substantially zero.

As a second parameter example the pulse sequence in FIG. 2b may have durations for the first, the second and the third pulse of 800 ms, 0.1 ms, and 0.1 ms respectively; a time between the first and the second pulse of 0.1 ms; and a time between the second and the third pulse of 5 ms. In this example the average gradient field strength of the second and the third pulse being substantially 4 000 times larger than the gradient field strength of the first pulse would result in the integral of gradient field strength over time for the gradient pulse sequence to be substantially zero.

Figure 3:
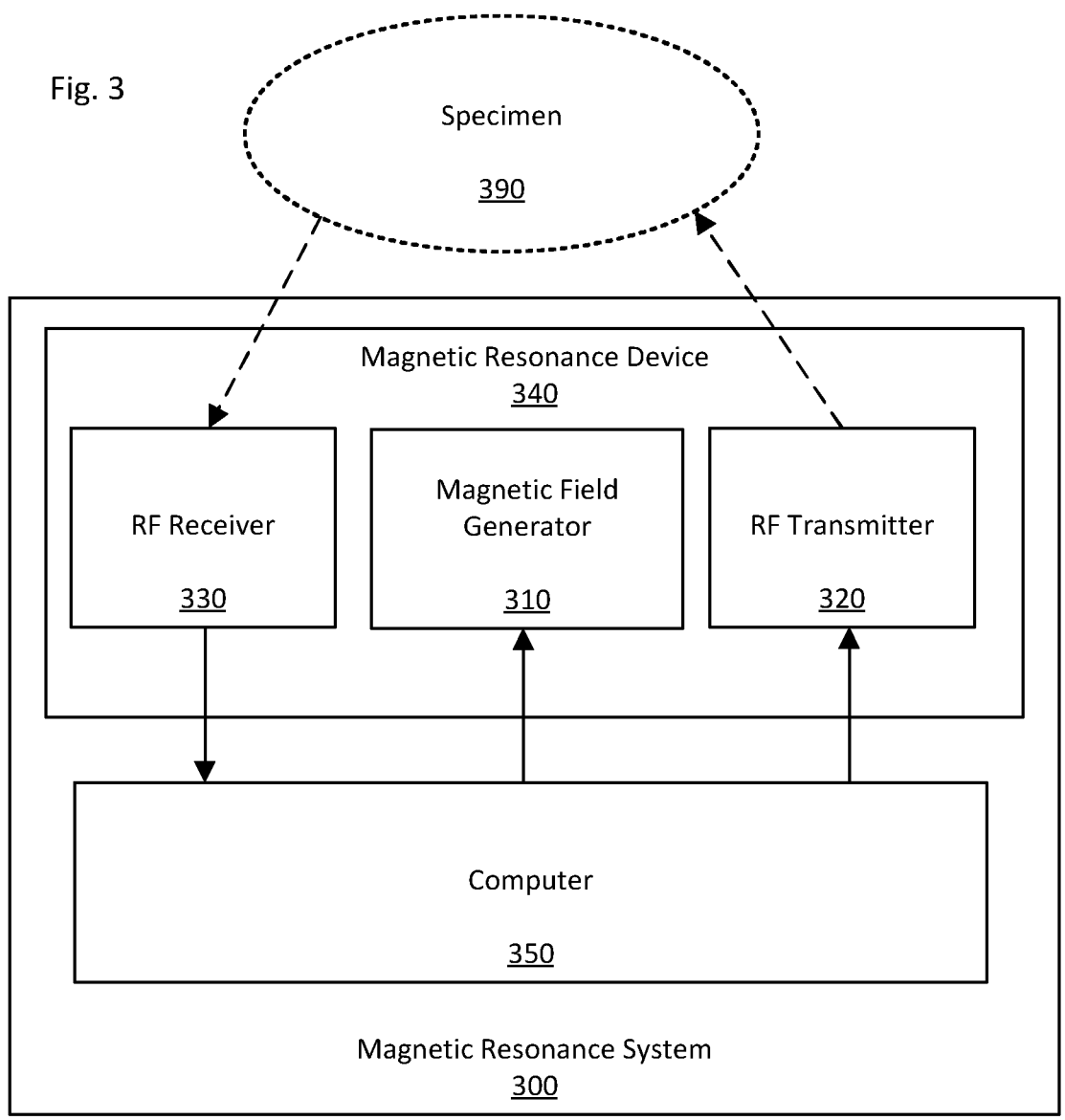
FIG. 3 depicts schematically a MR-based system for determining diffusion in a specimen

FIG. 3 depicts schematically a magnetic resonance based system for determining diffusion in a specimen. The system 300 comprises a magnetic resonance device 340, such as a magnetic resonance imaging scanner, and a computer 350. The magnetic resonance device 340 comprises a radiofrequency, RF, transmitter 320, a RF receiver 330 and a magnetic field generator 310. The RF transmitter 320 is arranged to project radio frequency pulses to a specimen 390. The RF receiver 330 is arranged to detect precessing magnetization in the specimen 390. The magnetic field generator 310 is arranged to project an adjustable magnetic field in the specimen 390. The computer is arranged to obtain information from the magnetic resonance device 340 and to control the magnetic resonance device 340.

The computer 350 is arranged to control the magnetic resonance device 340 to project at least one sequence of magnetic field gradient pulses and radiofrequency pulses into the specimen 390; and collect magnetic resonance measurement data from said specimen 390 at a plurality of different gradient durations, gradient strengths and gradient directions. The computer 350 is further arranged to reconstruct at least one Fourier transform for each at least one diffusion parameter based on the collected magnetic resonance measurement data; and determine the at least one diffusion parameter based on the corresponding reconstructed at least one Fourier transform, wherein each gradient pulse sequence comprises at least three gradient pulses wherein at least one gradient pulse is configured to introduce a phase shift in spin-labelled particles comprised in the specimen 390 based on position.

In some examples of the system 300, the computer 350 is arranged to project a gradient pulse sequence configured to introduce two phase shifts in spin-labelled particles comprised in the specimen 390, based on the particles' positions at two different times.

Figure 4:
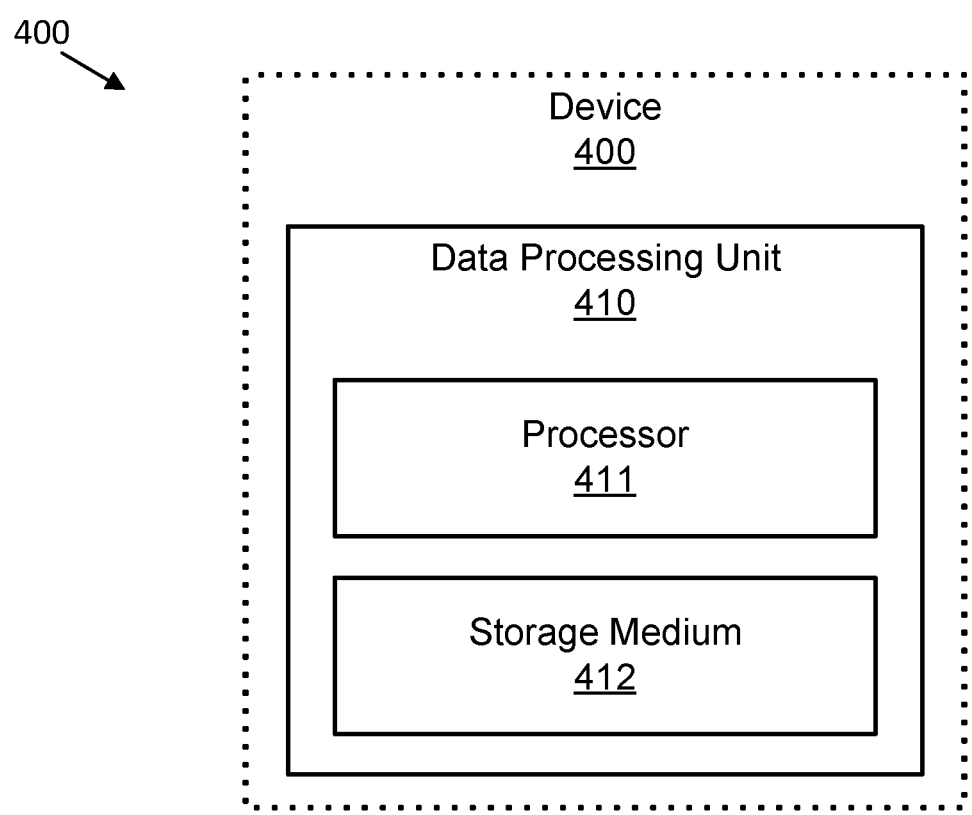
FIG. 4 depicts schematically a data processing unit comprising a computer program product.

FIG. 4 depicts schematically a data processing unit comprising a computer program product for determining a position and an orientation. FIG. 4 depicts a data processing unit 410 comprising a computer program product comprising a non transitory computer-readable storage medium 412. The non-transitory computer-readable storage medium 412 having thereon a computer program comprising program instructions. The computer program is loadable into a data processing unit 410 and is configured to cause a processor 411 to carry out the method for determining a position and an orientation accordance with the description of FIG. 3.

The data processing unit 410 may be comprised in a device 400, such a magnetic resonance based system.

Figure 5:
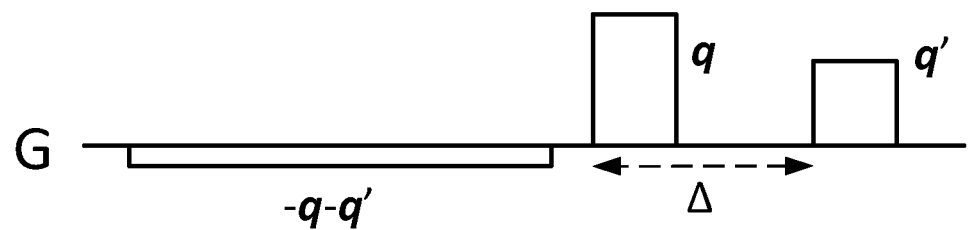
FIG. 5 depicts a proposed three pulse magnetic field gradient pulse sequence for an MR experiment.

FIG. 5 shows a magnetic field gradient pulse sequence (G). FIG. 5 depicts a proposed three pulse magnetic field gradient for an MR experiment. The example pulse sequence comprises three pulsed magnetic field gradients. q and q' are related to the gradient strength multiplied by the duration of the respective pulses, wherein A is the time between the start of the second pulse and start of the third pulse. In this example the sum of the gradient strength multiplied by the duration for all pulses is zero. In FIG. 5 the plotted gradient sequence is the effective one, that is, the directions of the particular gradient vectors reflect the effect of any RF pulse that may be present in the experimental design. For example, when there is only one 180 degree radiofrequency pulse in the sequence, the directions of all gradients applied before the said radiofrequency pulse would be reversed in the technique's implementation.

Figure 6:
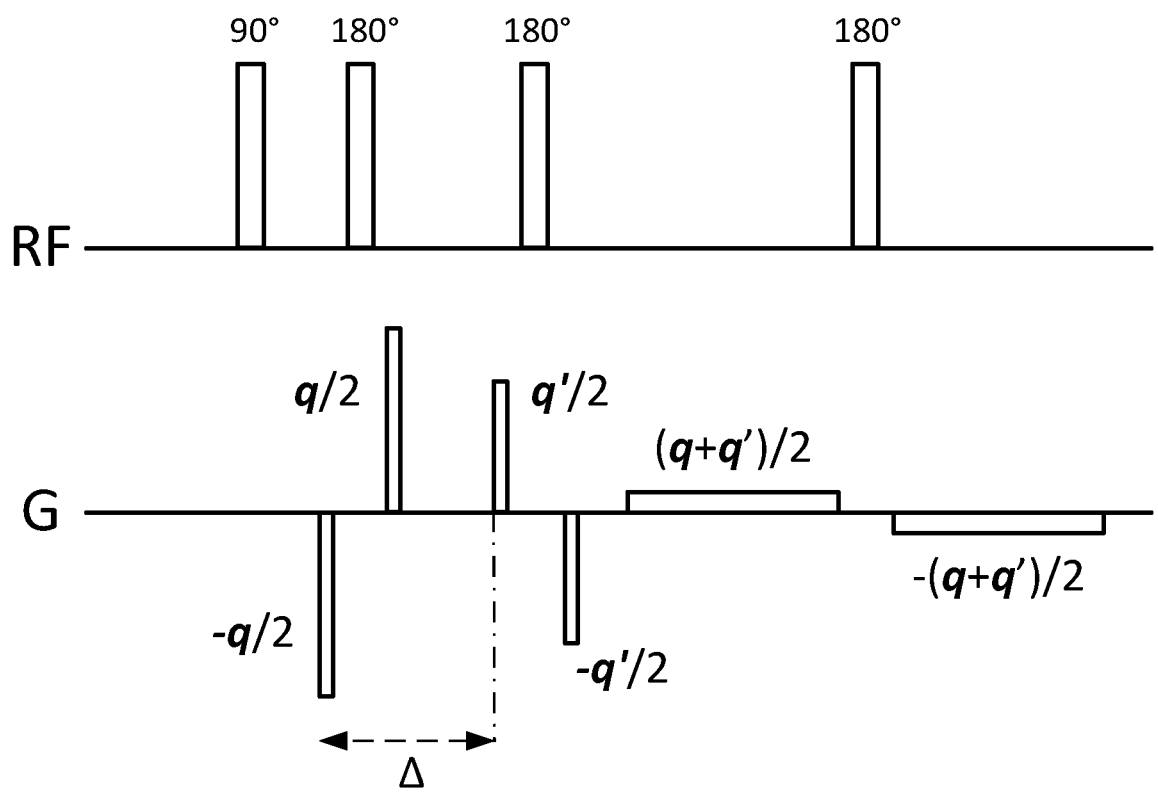
FIG. 6 depicts a particular embodiment of a pulse sequence featuring radiofrequency and gradient pulses

FIG. 6 shows a magnetic field gradient pulse sequence (G) and a radiofrequency pulse sequence (RF). FIG. 6 depicts a particular embodiment of the proposed technique wherein the shorter pulsed magnetic field gradients are applied before the longer pulsed magnetic field gradients. Moreover, each gradient is split into two, one before a 180 degree radiofrequency pulse, the other after the 180 degree radiofrequency pulse. Here, the parts before and after the 180 degree radiofrequency pulse are applied in opposite directions to account for the phase shift induced by the radiofrequency pulse. In this example A is the time between the starting times of the first pair of gradients and the second pair of gradients. q and q' are related to the gradient strength multiplied by the duration of the respective pulses.

Figure 7A:
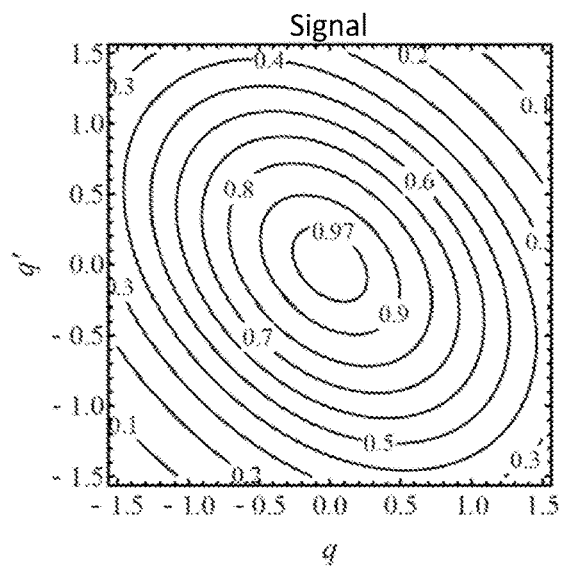
FIG. 7a-c depict contour plots indicative of acquired signal and determined diffusion propagator in a specimen.
Figure 7B:
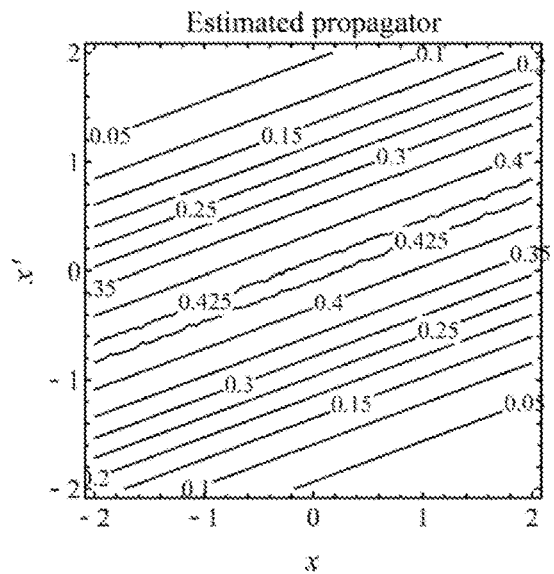
Figure 7C:
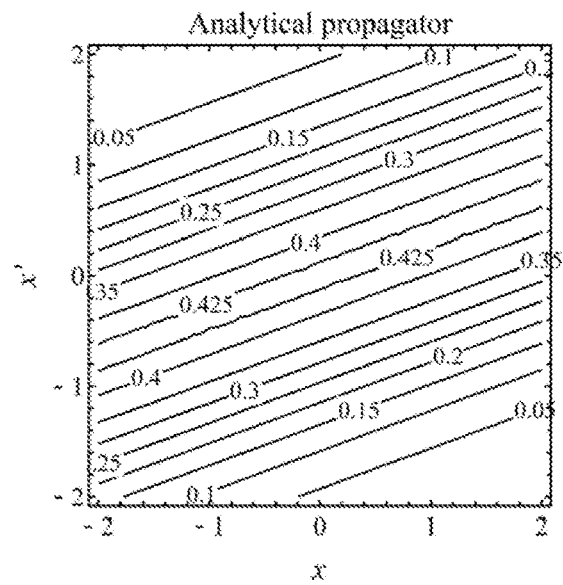

FIG. 7a-c depict contour plots indicative of acquired signal and determined diffusion propagator in a specimen. The example contour in FIG. 7a plots the signal plotted against q and q'. The contour plot in FIG. 7b depicts a determined diffusion propagator plotted against x and x' as shown. The contour plot in FIG. 7c represents an analytical form of the diffusion propagator, representing an analytical expression for the diffusion propagator for particles subject to a Hookean restoring force.

Figure 8A:
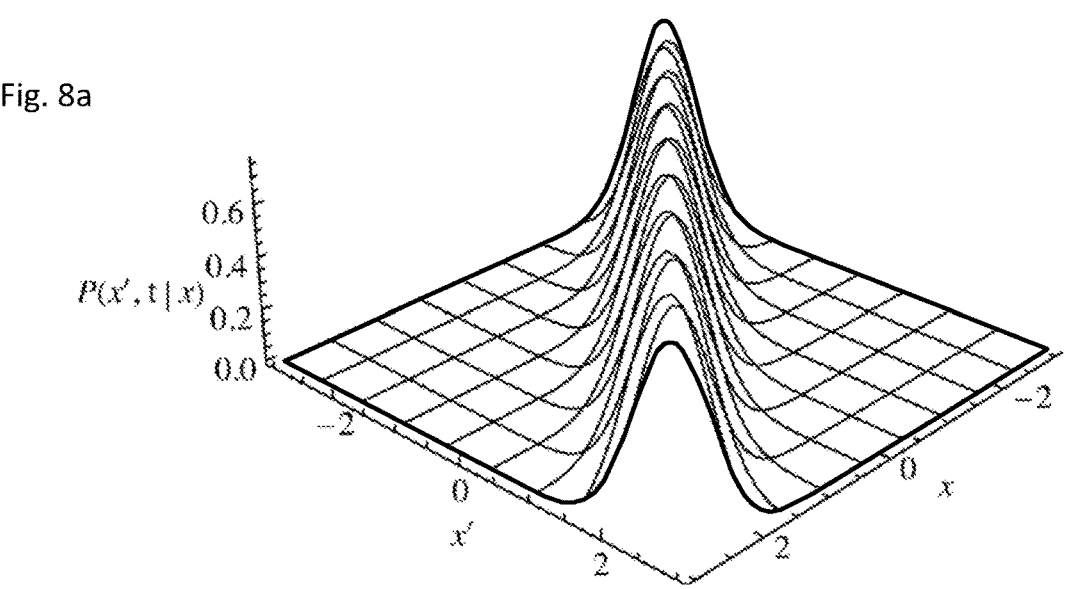
FIG. 8a-c depict surface plots indicative of determined diffusion propagator in a specimen.
Figure 8B:
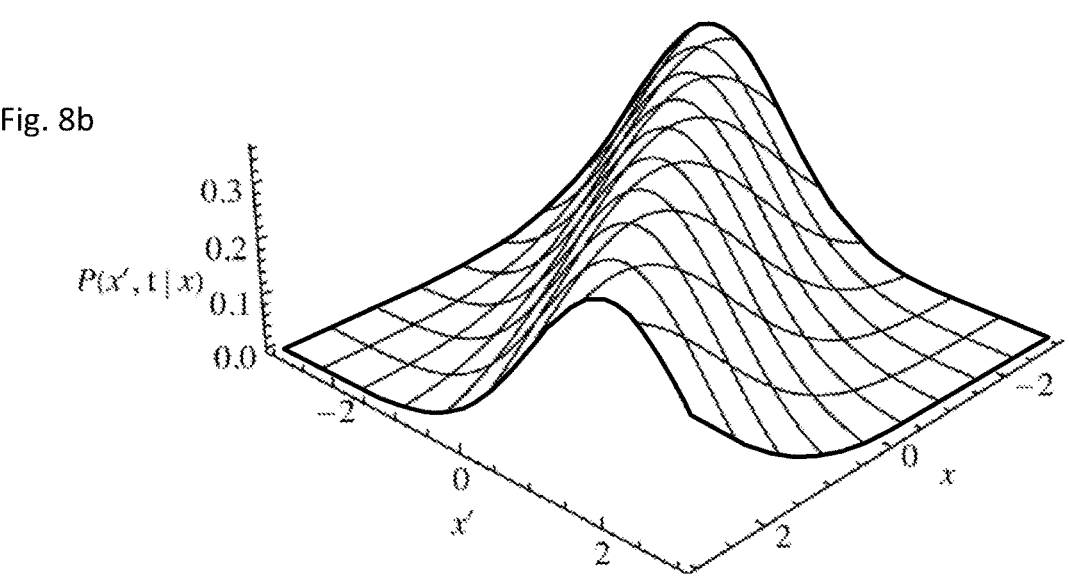
Figure 8C:
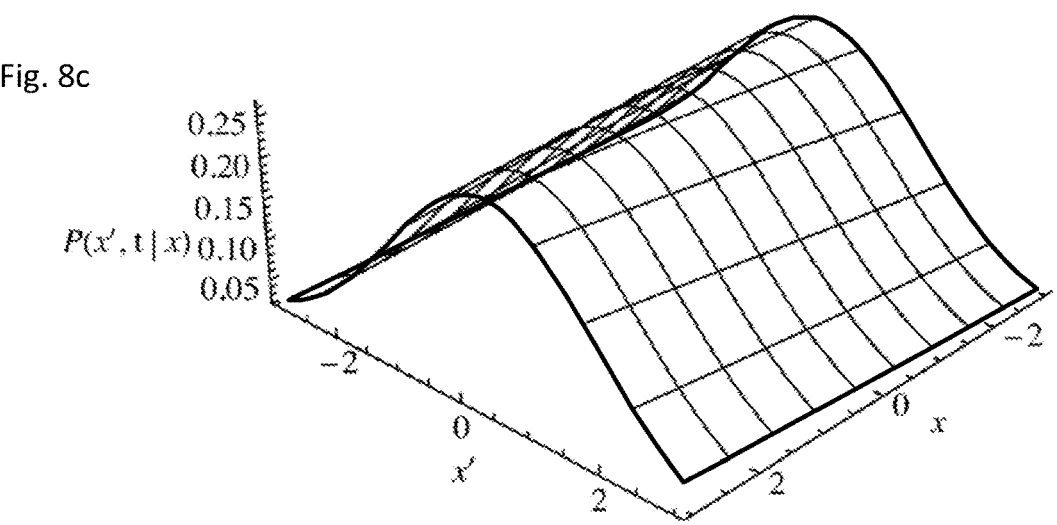

FIG. 8a-c depict surface plots indicative of determined diffusion propagator in a specimen. The surface plots representing the diffusion propagator estimated with increasing values of Δ. In this example the time between the last two pulses being 0.01 ms, 0.4 ms, and 10 ms, for FIGS. 8a, 8b and 8c respectively.

Figure 9A:
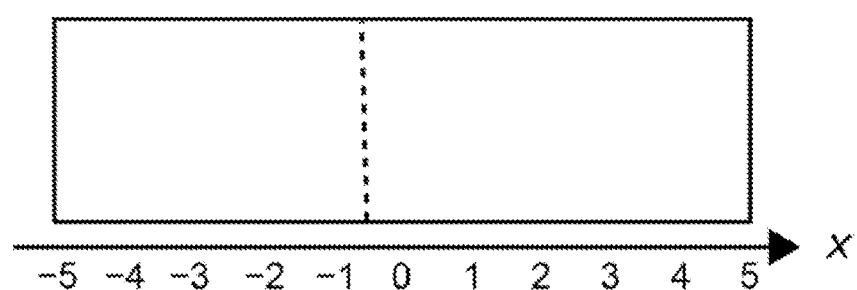
FIG. 9a-c depict schematically diffusion propagators for one-dimensional pores.
Figure 9B:
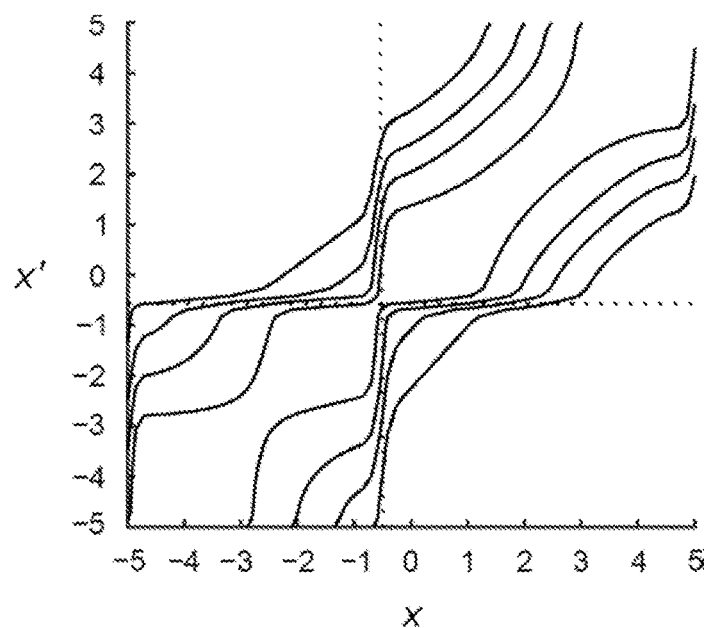
Figure 9C:
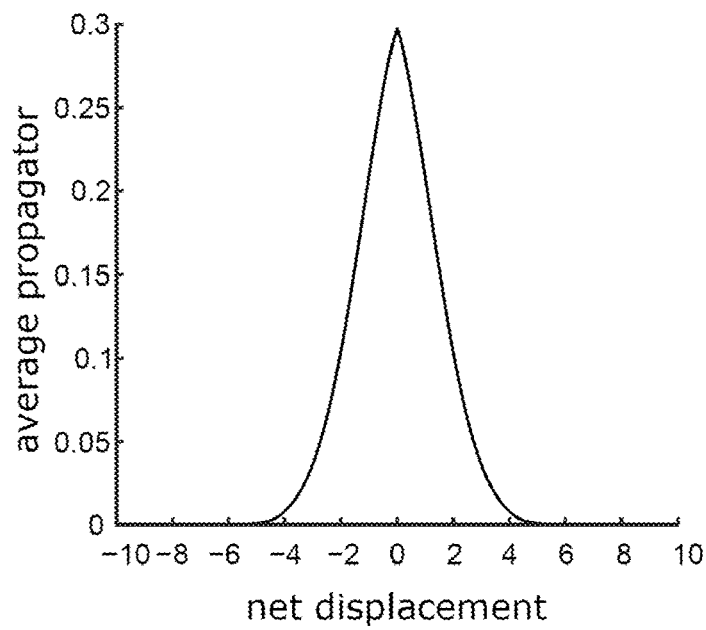

FIG. 9a-c depict schematically diffusion propagators for one-dimensional pores. The particular geometry is illustrated in FIG. 9a. Here, the dashed line indicates the position of the semipermeable membrane within a pore that is 10 units along the x direction. The gradients are applied in +x and −x directions. FIG. 9b depicts a contour plot of the hyperbolic tangent of the estimated propagator using the proposed method. FIG. 9c depicts the ensemble average propagator estimated from data acquired using the pulsed gradient spin echo (PGSE) (See E. O. Stejskal, and J. E. Tanner, J. Chem. Phys., 42, 288, (1965)) method.

Figure 10A:
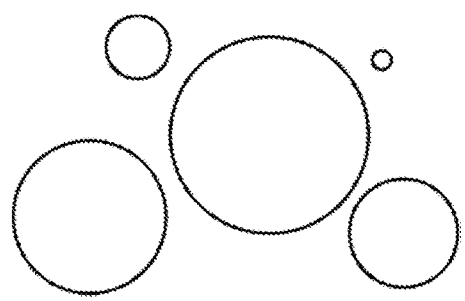
FIG. 10a-d depict schematically a specimen comprising five circular pores and quantities related to the heterogeneity of the specimen.
Figure 10B:
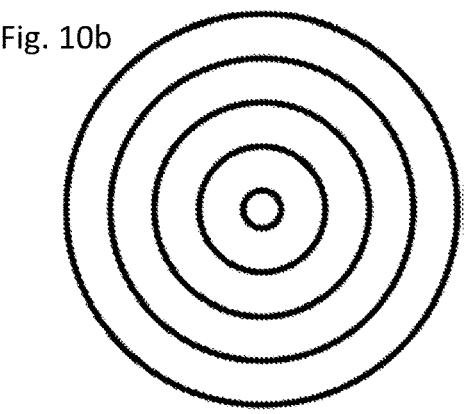
Figure 10C:
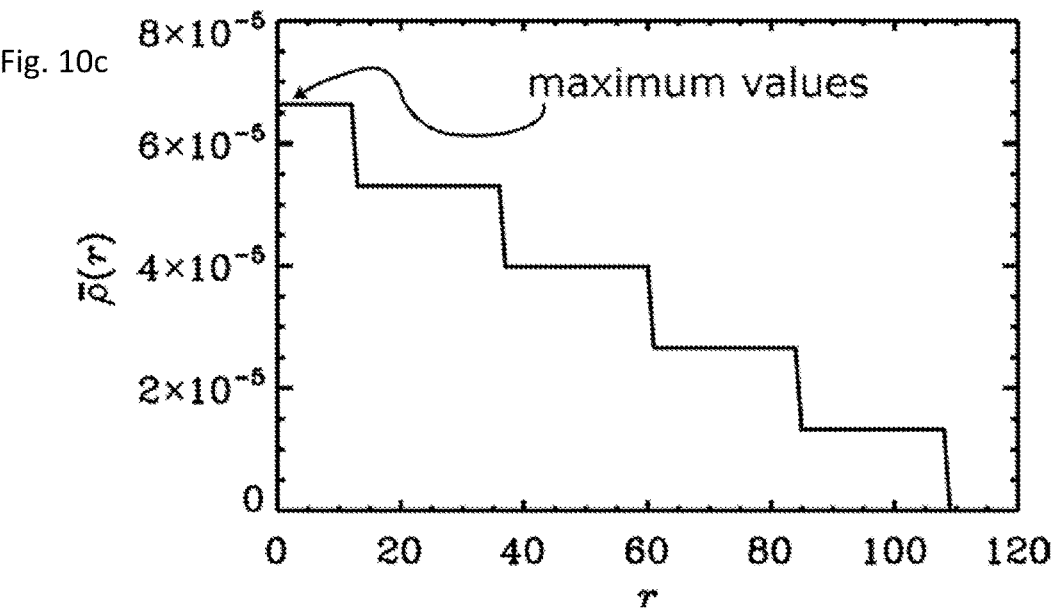
Figure 10D:
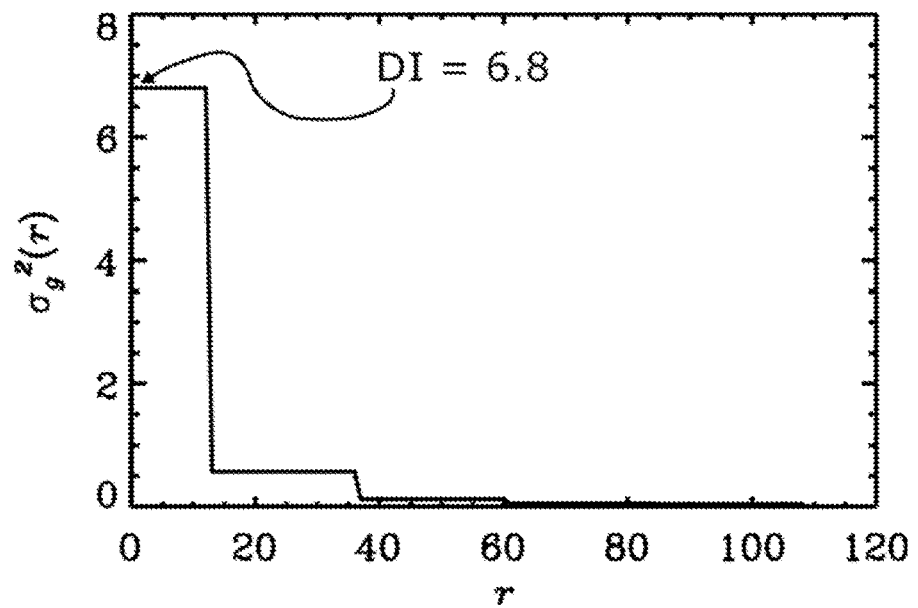

FIG. 10a-d depict schematically a specimen comprising five circular pores and quantities related to the heterogeneity of the specimen. FIG. 10a depicts the estimation of the dispersity index for a specimen comprising 5 circular pores of radii 12, 36, 60, 84, and 108 units. FIG. 10b depicts the same pores when their centres coincide. The technique effectively performs the measurement on the system depicted in FIG. 10b. The distance from the common centre in FIG. 10b is r. FIGS. 10c and 10d plot two quantities that can be obtained using the proposed method against r. The r value that maximizes the first quantity is employed to estimate the dispersion index as shown in FIG. 10d.

The invention relates to nuclear magnetic resonance (NMR) and magnetic resonance imaging (MRI) and, more particularly, to a method for measuring diffusion within specimens and for generating spectra and images related thereto.

Application of a plurality of magnetic field gradients provides an experimental tool to investigate the dependence of the MR signal on the diffusion-sensitizing gradient strength (G) and direction, diffusion gradient pulse duration ($\delta$) and time between the application of the two pulses ($\Delta$). The sensitivity of the MR measurements to variations in these parameters have been used to infer structural information from the observed sample. One way to characterize the diffusional process using methods that employ magnetic field gradients is to calculate diffusivity (or diffusion coefficient) that is related to the mobility of the diffusing molecules. The diffusion propagator $P(x',t|x)$ represents the probability that a particle located at position x travels to x' over a time interval of duration t. This quantity fully describes the diffusional motion in simple as well as complicated environments, which could feature restricting or semipermeable walls, external forces, spatially and temporally varying diffusivity, etc.

q-space NMR and q-space MRI are spectroscopy and imaging modalities that enable the measurement of displacement probabilities noninvasively. According to this approach, the signal is observed at a plurality of q values (or vectors), where q is a quantity proportional to $\delta$, and G. The inverse Fourier transform of the resulting array of signal values gives the ensemble averaged propagator, which is the average net displacement probabilities of the particles in space. The ensemble average propagator is represented as a function of the net displacements and experimental parameters, such as q, $\delta$, G, $\Delta$. The ensemble average propagator is related to the diffusion propagator through an integration over one of the position variables of the diffusion propagator.

A computer-implemented diffusion magnetic resonance (diffusion-MR) system and method examines specimens such as materials, porous media, food products, and biological tissue by detecting diffusion in the specimen. A pulse sequence featuring gradients of different durations applied at different times employed with an arrayed plurality of different diffusion gradient durations, strengths, and directions collectively provide a Fourier transform of the diffusion propagator. MR diffusion data is collected from the specimen. The diffusion propagator is computed by transforming the data on a computer. The data is used to estimate the steady state particle distribution and other measures. The calculated propagator and measures can be used to create new contrasts in MR imaging that can detect changes in the specimen's microstructure and improve the sensitivity and specificity of MR studies for clinical applications.

An object of the present invention is to quantify the diffusive motion of the particles. A further object of the present invention is to provide new NMR and MRI techniques that use information contained in the measured diffusion and characterize its evolution in time.

A method and system for measuring the diffusion propagator of spin-labelled particles is described herein. A pulse sequence is applied using an NMR spectrometer or imager to a sample within the NMR apparatus for generating NMR signals from which the diffusion propagator and related quantities can be calculated. The MR diffusion data are preferably acquired from the tissue at an arrayed plurality of pulse sequences with different diffusion gradient durations, strengths, and/or directions. A computer-implemented diffusion magnetic resonance (diffusion-MR) method analyses a specimen such as a material or porous medium or biological tissue by detecting diffusion in the specimen.

Calculated MR characteristics are preferably visualized on multi-dimensional plots where spatial coordinates are displayed on different axes. At least one quantity describing the diffusion propagator is calculated using the computer from the MR diffusion data. The estimated propagator may be related to the microstructure of the medium. Spatial images of such quantities describing the underlying diffusion process can be produced and can be related to other structural characteristics within each voxel. Diffusion data obtained using measurements performed with different diffusion gradients are plotted and analysed. The propagators are displayed with contour lines or surfaces. Diffusion measurements may also be employed in calibrating the NMR apparatus itself.

Brief description of the drawings, FIGS. 5, 7 and 8. There are shown in the drawings embodiments which are presently preferred, it being understood, however, that the invention can be embodied in other forms without departing from the spirit or essential attributes thereof.

FIG. 5 shows one embodiment of the sequence of gradient pulses to be incorporated into a MR pulse sequence for achieving sensitivity to diffusion propagator. The horizontal direction indicates time so that in this particular embodiment, three gradient pulses are applied at different times. The height of the boxes indicate the strengths of the gradients, which are to be varied in different repetitions of the experiment. When the radiofrequency pulses are applied, the direction of the gradients are altered to achieve similar information. Some of the gradient pulses may be applied before or after the radiofrequency (RF) pulses. Any one of the gradient pulses can be split so that a part of that gradient pulse is applied before an RF pulse while another part is applied after the RF pulse.

FIG. 7a-c show one embodiment of the results displayed as contour plots. The panel on the left depicts the signal computed for diffusion subject to a restoring force as described in (Yolcu et al., Phys Rev E, 93, 052602, 2016) computed with the parameters: diffusion coefficient=2 $\mu m^2$/ms, confinement=0.5 $\mu m^{-2}$, duration of the first pulse=300 ms, delay between the first and second pulses=0.1 ms, duration of the second pulse and the third pulse=0.0001 ms, time between the last two pulses=1 ms. The panel in the middle shows the propagator computed from this signal profile using the invention described here. The panel on the right depicts the analytical expression for the diffusion propagator for particles subject to a Hookean restoring force.

FIG. 8a-c show one embodiment of the results displayed as surface plots. The same method as in FIG. 7a-c is employed with: diffusion coefficient=2 $\mu m^2$/ms, confinement=0.5 $\mu m^{-2}$, duration of the first pulse=10 ms, delay between the first and second pulses=0.1 ms, duration of the second pulse and the third pulse=0.1 ms, time between the last two pulses=0.01 ms (left), 0.4 ms (middle), and 10 ms (right). In all panels the diffusion propagator was computed using the invention described here.

A computer-implemented diffusion magnetic resonance (diffusion-MR) method analyses materials, porous media, and biological tissue by detecting diffusion in the specimens or patients. A mathematical relationship is provided, where a function describing the movements of particles is computed from the acquired data. MR diffusion data is collected from the specimen. The MR diffusion data is preferably acquired from the specimen with an arrayed plurality of acquisitions with different diffusion gradient durations, strengths, and directions.

The MR diffusion data can be collected using magnetic resonance spectroscopy, localized magnetic resonance spectroscopy, or magnetic resonance imaging (MRI). Data signals associated with different ones of the plurality of diffusion gradients correspond to different properties for the diffusional process in the specimen being examined.

Definitions: Unless defined otherwise, all technical and scientific terms used herein have the meaning commonly understood by a person having ordinary skills in the art to which this invention belongs. As used herein, the following terms have the meanings ascribed to them unless specified otherwise.

As used herein, the term magnetic resonance (MR) device incorporates all devices capable of magnetic resonance spectroscopy, MR imaging, similar techniques such as electron paramagnetic resonance, electron spin resonance, or equivalents. The methods of the invention can be practiced using any such device, or variation of an MR device or equivalent, or in conjunction with any known MR methodology. In magnetic resonance methods and apparatus, a static magnetic field is applied to a specimen, tissue, or a body under investigation in order to define an equilibrium axis of magnetic alignment in a region of interest. A radio frequency field is then applied to that region in a direction orthogonal to the static magnetic field direction in order to excite magnetic resonance in the region. When spatial information is desired, carefully designed sequences of magnetic field gradients are applied that makes localized MR spectroscopy and MR imaging possible. The resulting signals are detected by radio-frequency coils placed adjacent the tissue or area of the body of interest.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

The methods of the invention include MRI diffusion-weighted imaging (DWI). Briefly, this approach is based on the measurement of random motion of molecules and the capability of nuclear magnetic resonance to quantify diffusional movement of particles. Diffusion imaging is a method that combines this diffusion measurement with MRI. This technique can characterize diffusion properties of spin-labelled molecules at each picture element (pixel or voxel) of an image. Properties of the diffusion of spin labelled molecules are related to the chemical and geometrical environments. For example, diffusion imaging can be used to infer information regarding the microstructure (e.g., cellular membranes and large macromolecules) that restrict or hinder the water molecular motion. Consequently, diffusion imaging can detect water diffusion in highly ordered organs, such as brains. In these tissues, water does not diffuse equally in all directions due to restrictions of water molecules imposed by cellular membranes, resulting in a property called anisotropic diffusion.

By considering MR data obtained with special gradient pulse sequences, it has been discovered that diffusion within the specimen can be characterized by estimating the diffusion propagator. The obtained diffusion propagator can represent different phenomena. For example, in the embodiment illustrated in FIG. 5, when the first pulse is very long and the second and third pulses are very short, the obtained estimate of the diffusion propagator provides an accurate representation of the real diffusion propagator. When the pulse durations differ from the said conditions, the invention can still be employed and the obtained quantity represents an apparent diffusion propagator, which may not represent the true diffusion propagator. For example, when the durations of the second and third pulses in FIG. 5 are finite, the arguments of the estimated diffusion propagator, x and x', represent the particle positions averaged over the duration of the gradients.

This new method for measuring diffusion provides previously undiscovered information about the specimen that can be used to generate data and images from the data and obtain new contrasts based on different mathematical parameters. These new contrast mechanisms should provide additional information about the material or tissue microstructure that can improve the specificity and utility of diffusion MR for characterizing alterations, e.g. due to disease in human patients. The method can be practiced in vitro, ex vivo or in vivo.

An MR system including an MR magnet and its operating/analysis software can be configured to collect MR signals from the specimen at a plurality of different diffusion gradients, gradient durations, and diffusion times. Such MR signals can be transformed into diffusion propagators within particular materials or tissues of human or animal subjects. The system and computer software can acquire, organize, analyse, and parameterize diffusion using a computer.

The system can be embodied as a magnetic resonance imaging or spectroscopy system and software for acquiring, organizing, analysing and parameterizing diffusion data and transform it into the diffusion propagator. Applied to diffusion MRI, although current diffusion MRI contrast mechanisms can provide sensitive detection of many diseases, they are often unable to distinguish particular disease processes that need to be treated differently (e.g. tumour from edema). A system according to the invention can provide several new MRI diffusion contrast mechanisms that will provide better specificity for particular disease processes. Thus, the invention can improve the utility of diffusion MRI for evaluating clinical patients.

By detecting changes in diffusion in a tissue, the invention provides previously unattainable contrast for detecting changes in the microstructure of those materials tissues or organs. The methods of the invention also provide methods for monitoring changes in the physiology or the health of a collection of cells or a tissue. These methods can be particularly useful for monitoring the effectiveness of a treatment or a process such as development and aging. Contrast-mechanisms based on this invention should provide additional information about tissue microstructure that may improve the clinical specificity and clinical utility of diffusion MRI for characterizing disease in human patients.

By detecting the likelihood of movements between different points in space, the method may be instrumental in assessing the connectivity patterns in fibrous specimens. In particular, it may be possible to differentiate crossing, splaying, and kissing fibre compositions using the method.

By detecting changes in the structure of porous media, the porosity and connectedness of the medium could be evaluated, which may be useful in evaluating the ease with which fluids, such as water and hydrocarbons, can be recovered from such media.

By detecting diffusion within and around globules within suspensions or emulsions, the method may be instrumental in assessing the quality of food products.

The invention can be applied to any biological tissue in human, animal or plant subjects (e.g. nervous, cardiac or muscle tissue from rats, mice or humans). The data may be acquired from in vivo, ex vivo, cultured or post mortem tissue. This application also can be used for simulated tissue or artificial tissue models, such as red blood cell ghosts, tissue slices or cell cultures (with cells originally acquired from biological tissue).

The invention can also be used to distinguish healthy from pathologically injured tissue. Pathological tissue includes, but is not limited to cancerous, ischemic, traumatized, chronically injured or degenerative tissue. This application can also be used to study genetically-altered tissue. This application also can be used to recognize or characterize the similarity of diffusion in tissue substitutes or replacements (such as stem cells, organ transplants or tissue created by 3D scaffolds) to diffusion in normal, healthy tissue.

The invention can also be used to calibrate the MR apparatus itself. This can be done by measuring the diffusion propagator in simple systems such as free water. In this case, the diffusion process is known to be Gaussian. Therefore, acquisition of a series of diffusion weighted data from such a sample can give accurate information about the accuracy of the gradient timings.

Acquisition of a series of diffusion weighted data from such a sample may determine information about the accuracy of the applied methods, and hardware performance.

Examples determining diffusion. The following section is based on the pulse sequence in FIG. 5 provided to illustrate, but not to limit the claimed invention.

A pulse with long duration is employed so that the integral of the waveform vanishes, and contributions from all domains making up the specimen are independent of their position within the sample. The two subsequent pulses q and q' introduce phase shifts that depend on the particles' average positions (averaging performed over the pulses' duration), denoted by x and x', respectively. The q has d components, which is the number of dimensions in which the diffusion process is to be measured. The signal attenuation (actual signal divided by the signal when no diffusion gradient is applied) is then related to the propagator $P(x',\Delta|x)$ and the steady-state distribution $\rho(x)$ through the relationship $$E_\Delta(q,q') = \int dx \rho(x) \int dx' P(x',\Delta|x) e^{-i(q \cdot x + q' \cdot x')} \quad \text{(Eq. 1)}$$

The propagator can be obtained via the 2d-dimensional inverse Fourier transform of the signal $$P(x', \Delta | x) = \frac{\rho(x)^{-1}}{(2\pi)^{2d}} \int dq\, e^{iq \cdot x} \int dq' e^{iq' \cdot x'} E_\Delta(q, q') \quad \text{(Eq. 2)}$$

along with an estimate of $\rho(x)$, which is the propagator at long diffusion time, made available by transforming either the subset of the data with q'=0 or data obtained at long $\Delta$ with q=q' through the expressions $$\rho(x) = \frac{1}{(2\pi)^d} \int dq\, e^{iq \cdot x} E_\Delta(q, 0) \quad \text{(Eq. 3)}$$

$$\rho(x) = \frac{1}{(2\pi)^d} \int dq\, e^{iq \cdot x} (E_\infty(q, q))^{1/2} \quad \text{(Eq. 6)}$$

In the case of a structurally heterogeneous specimen comprising N isolated pores, the 2d-dimensional inverse Fourier transform of $E_\Delta(q, q')$ yields $\Sigma_{n=1}^{N} f_n\, \rho_n(x)\, P_n(x', \Delta|x)$, where $f_n$ denotes the signal fraction contributed by the nth pore to the signal when the gradients are turned off. At long $\Delta$, the quantity $\Sigma_{n=1}^{N} f_n\, \beta_n(x)^2$ can be obtained by setting x=x'. On the other hand, the d-dimensional inverse Fourier transform of $E_\Delta(q, 0)$ is $\Sigma_{n=1}^{N} f_n\, \rho_n(x)$. The square of the last quantity is equal to the previous one for monodisperse systems and their dissimilarity can be employed to measure dispersity at different positions in space when the centres-of-mass of all pores are brought to the same point.

The diffusion propagator can be obtained via the 2d-dimensional inverse Fourier transform of the signal $$P(x', \Delta | x) = \frac{\rho(x)^{-1}}{(2\pi)^{2d}} \int dq\, e^{iq \cdot x} \int dq' e^{iq' \cdot x'} E_\Delta(q, q') \quad \text{(Eq. 2)}$$

along with an estimate of $\rho(x)$, which is the diffusion propagator at long diffusion time, made available by transforming either the subset of the data with q'=0 or q=0' through the expressions $$\rho(x) = \frac{1}{(2\pi)^d} \int dq\, e^{iq \cdot x} E_\Delta(q, 0) \quad \text{(Eq. 3)}$$

$$\rho(x) = \frac{1}{(2\pi)^d} \int dq' e^{iq' \cdot x} E_\Delta(0, q') \quad \text{(Eq. 4)}$$

Thus, the diffusion propagator can be obtained through $$P(x', \Delta | x) = \frac{\int dq\, e^{iq \cdot x} \int dq' e^{iq' \cdot x'} E_\Delta(q, q')}{(2\pi)^d \int dq\, e^{iq \cdot x} E_\Delta(q, 0)} \quad \text{(Eq. 5)}$$

Several quantities relevant to the microscopic structure of the specimen can be estimated using the proposed experimental technique. For example, the quantity $W(x', \Delta; x, 0)$ denotes the joint distribution for a particle being at position x at a certain time and at a position x' at a duration $\Delta$ later. This joint density is readily available using the invention through the Fourier relationship $$W(x', \Delta; x, 0) = \frac{1}{(2\pi)^{2d}} \int dq\, e^{iq \cdot x} \int dq' e^{iq' \cdot x'} E_\Delta(q, q'). \quad \text{(Eq. 7)}$$

A 2d-dimensional vector K can be constructed having elements of q followed by the elements of q'. Similarly, a 2d-dimensional vector Y can be constructed having elements of x followed by the elements of x'. The signal attenuation or its logarithm can be expanded in a Maclaurin series in K. For example, the equation below determines the low-K behavior of the signal attenuation.

$$E_\Delta(K) \approx -\frac{1}{2}\sum_{k,l=1}^{2d} A_{kl}K_kK_l + \qquad \text{(Eq. 8)}$$

$$\frac{i}{6}\sum_{k,l,m=1}^{2d} A_{klm}K_kK_lK_m + \frac{1}{24}\left\{\sum_{k,l,m,n=1}^{2d} A_{klmn}K_kK_lK_mK_n\right\}$$

where $K_{kl}=\langle Y_kY_l\rangle$, $K_{klm}=\langle Y_kY_lY_m\rangle$, and $K_{klmn}=\langle Y_kY_lY_mY_n\rangle - 3\langle Y_kY_l\rangle\langle Y_mY_n\rangle$ are tensors that describe the cumulants of the position of the particles at two times separated by the time interval $\Delta$. These cumulant tensors can be estimated from the data collected using the invention by employing one of the many numerical model fitting techniques such as least squares estimation.

Another example involves a structurally heterogeneous specimen comprising N pores. In this case, the steady state distribution of particles in nth pore can be denoted by $\rho_n(x)$. Furthermore, $f_n$ denotes the signal fraction contributed by the nth pore to the signal when the gradients are turned off. The d-dimensional inverse Fourier transform of $E_\Delta(q, 0)$ or $E_\Delta(0, q')$ is $$\overline{\rho}(x) = \frac{1}{(2\pi)^d}\int dq\, e^{iq\cdot x}E_\Delta(q, 0) = \sum_{n=1}^N f_n\rho_n(x). \qquad \text{(Eq. 9)}$$

which integrates to unity. On the other hand, the 2d-dimensional inverse Fourier transform of $E_\Delta(q, q')$ yields $$\frac{1}{(2\pi)^{2d}}\int dq\, e^{iq\cdot x}\int dq'\, e^{iq'\cdot x'}E_\Delta(q, q') = \sum_{n=1}^N f_n\rho_n(x)P_n(x', \Delta\,|\,x). \qquad \text{(Eq. 10)}$$

At long $\Delta$, by setting x=x', the above quantity becomes $$\mu_2(x) = \frac{1}{(2\pi)^{2d}}\int dq\, e^{iq\cdot x}\int dq'\, e^{iq'\cdot x}E_\Delta(q, q') = \sum_{n=1}^N f_n\rho_n(x)^2. \qquad \text{(Eq. 11)}$$

A quantity, which can be referred to as "local variance" can be defined through $\sigma^2(x)=\mu_2(x)-\overline{\rho}(x)^2$. The square root of this quantity ("local standard deviation") can be made dimensionless through $\sigma_l(x)=\sigma(x)/\overline{\rho}(x)$, or via $\sigma_g(x)=\sigma(x)/\overline{\rho}(x_0)$, where $x_0$ can be taken to be any point with no vanishing $\overline{\rho}(x_0)$. A particular choice of $x_0$ is the one that maximizes $\overline{\rho}(x_0)$. These maps are expected to be descriptive of the space-dependent heterogeneity of the specimen when the centers-of-mass of all pores are brought to the same point.

In many scenarios, the steady state distribution for the nth pore, $\rho_n(x)$, is the indicator function of the pore space within which its value is the reciprocal of the pore volume, i.e., $\rho_n(x)=V_n^{-1}$ and vanishes outside the pore space. Ignoring possible relaxation differences, the signal fraction of the nth pore is $f_n=V_n/(\Sigma_n f_n V_n)$. Under these conditions, $\mu_2(x)$ integrates to the reciprocal of the mean pore volume indicated by $\langle V\rangle^{-1}$, which is also equal to $\overline{\rho}(x_0)$ when $x_0$ lies within all pores when their centres of mass are brought to the origin. This point can be determined to be any point that maximizes $\overline{\rho}(x)$. On the other hand, $\mu_2(x_0)=\langle V^{-1}\rangle\langle V\rangle^{-1}$. Of particular interest is the quantity $$DI = \sigma_g^2(x_0) = \sigma_l^2(x_0) = \frac{\sigma^2(x_0)}{\overline{\rho}(x_0)^2} = \frac{\mu_2(x_0)}{\overline{\rho}(x_0)^2} - 1 = \langle V^{-1}\rangle\langle V\rangle - 1, \qquad \text{(Eq. 12)}$$

which is referred to as "dispersity index" as it vanishes when all pores are of the same volume (irrespective of their orientation) and larger otherwise. DI can thus be computed from the data acquired through the introduced method using the expression $$DI = \frac{\int dq\, e^{iq\cdot x_0}\int dq'\, e^{iq'\cdot x_0}E_\Delta(q, q')}{\left(\int dq\, e^{iq\cdot x_0}E_\Delta(q, 0)\right)^2} - 1 \qquad \text{(Eq. 13)}$$

Yet another quantity that can be computed from the data is the distribution of the quantity $$u = \frac{x+x'}{2},$$

which is the average of the particle's positions during the application of the two shorter pulses. The distribution of u is defined to be $$\overline{P}(u)=2\int\rho(x)P(2u-x,\Delta|x)dx \qquad \text{(Eq.14)}$$

which can be obtained from the data via the following inverse Fourier transform $$\overline{P}(u) = \frac{1}{(2\pi)^d}\int dQ\, e^{iQ\cdot u}E_\Delta(Q/2, Q/2). \qquad \text{(Eq. 15)}$$

This concerns a particular realization of the proposed pulse sequence when Q/2=q=q'. The signal attenuation, or its logarithm can be expanded in a Maclaurin series in q. For example, the equation below determines the low-Q behavior of the signal attenuation.

$$\ln E_\Delta(Q/2, Q/2) \approx -\frac{1}{2}\sum_{k,l=1}^{d} C_{kl}Q_kQ_l + \qquad \text{(Eq. 16)}$$

$$\frac{i}{6}\sum_{k,l,m=1}^{d} C_{klm}Q_kQ_lQ_m + \frac{1}{24}\left\{\sum_{k,l,m,n=1}^{d} C_{klmn}Q_kQ_lQ_mQ_n\right\}$$

where $C_{kl}=\langle u_ku_l\rangle$, $C_{klm}=\langle u_ku_lu_m\rangle$, and $C_{klmn}=\langle u_ku_lu_mu_n\rangle - 3\langle u_ku_l\rangle\langle u_mu_n\rangle$ are tensors that describe the cumulants of the average position of the particles. These cumulant tensors can be estimated from the data collected using the invention by employing one of the many numerical model fitting techniques such as least squares estimation.

Magnetic resonance data acquisition. Options for MR data acquisition are not limited to the experiment above. For example, spectroscopy, localized spectroscopy, and imaging methods can also be employed. The order of long and short pulses can be changed. Each pulse can be replaced with a plurality of pulses. The pulses do not have to be constant during their application; their intensity can vary in time. In this case, q and q'-values are defined through the expression $$q = \gamma \int G(t) dt, \quad (Eq.17)$$

$$q' = \gamma \int G'(t) dt, \quad (Eq.18)$$

where γ is the gyromagnetic (magnetogyric) ratio of the particles being examined, G(t) and G'(t) are the effective gradient vectors (after the effects of radiofrequency pulses are accounted for) for the respective gradient pulses, and the integrals are calculated over the durations of the respective gradients.

MR data needed for the computation of the diffusion propagator can be obtained from diffusion-sensitized acquisitions with a plurality of q and q'-values (which can be obtained by changing the gradients' strength, direction, and/or diffusion pulse duration). A particular sampling scheme of the q-space is not required and many different alternatives could be employed to obtain the propagator and characterize the diffusion process in accordance with the present invention. The data acquisition can be performed at a plurality of gradient separations (such as Δ) and durations.

The pulse sequence used can be selected from one of many possibilities, such as those utilizing spin echoes, stimulated echoes, gradient echoes, or free induction decays. Also, fast imaging techniques such as echo planar imaging can be employed in accordance with the present invention.

Construction of the diffusion propagator. The process of computing the propagator for diffusion in the specimen involves the evaluation of a transform of the observed signal attenuations. As mentioned previously, the reconstruction scheme described above involves an inverse Fourier transform. The Fourier and related transforms such as sine and cosine transforms along with their inverses can be computed on a computer or evaluated analytically for some systems. On the computer, the transform can be performed by discrete Fourier transform (DFT) and related algorithms such as the fast Fourier transform (FFT) and their inverses.

Example embodiments. A first example is a diffusion magnetic resonance (diffusion-MR) method for analysing specimens such as materials, porous media, food products, and biological tissue by detecting diffusion, comprising the steps of:
  providing a computer program of a pulse sequence to be run on a computer controlling the MR scanner wherein the data are obtained by applying gradient pulses of different duration, strength and/or direction to encode the particles' positions at different times;
  providing a model of the diffusion signal relating it to the diffusion propagator through a Fourier transform,
  collecting MR diffusion data from said specimen, calculating using a computer at least one Fourier or sine or cosine transform or their inverses relating to said data obtained by applying said acquisition protocol to said specimen,
  calculating, using a computer, measures related to the diffusion characteristics of the specimen.

A second example is the first example wherein said MR diffusion data is acquired from said specimen using said pulse sequence featuring an arrayed plurality of different diffusion, gradient strengths, gradient directions, gradient durations and diffusion times.

A third example is the first example wherein said MR diffusion data is collected in said collecting step using magnetic resonance imaging, magnetic resonance spectroscopy or localized magnetic resonance spectroscopy.

A fourth example is the first example wherein said pulse sequence comprises at least three gradient pulses used for measuring diffusion and one of the said gradient pulses is longer than another one of the said gradient pulses.

A fifth example is the first example wherein said Fourier transform is calculated using analytical derivations, discrete Fourier transform or fast Fourier transform to obtain the diffusion propagator or related quantities.

A sixth example is the first example wherein said pulse sequence is employed to obtain measures comprising the dispersity of domain shapes.

A seventh example is the first example wherein said pulse sequence is employed to obtain the steady state distribution of particles.

An eighth example is the second example further comprising the step of imaging said tissue from said MR data collected at said plurality of diffusion gradient durations, gradient strengths, gradient directions and times using said computer, wherein said plurality of said diffusion gradients measure the Fourier transform of the diffusion propagator.

A ninth example is the first example wherein said MR diffusion data is collected from materials, porous media, soft-matter, food products, in vivo, ex vivo, cultured or post mortem biological tissue, simulated materials, simulated tissue, synthetic materials, artificial tissue models, tissue slices or cell cultures.

A tenth example is the first example wherein said MR diffusion data is used to distinguish healthy from pathological tissue, study genetically-altered tissues, tissue substitutes and replacements.

An eleventh example is the first example wherein said diffusion propagator and related measures are used to calibrate said MR apparatus.

A twelfth example is a diffusion MR-based system for analysing diffusion in material specimens and biological tissue, comprising:
a MR device, wherein said MR device projects a sequence of magnetic field gradient pulses and radiofrequency pulses to said tissue and collects MR diffusion data from said specimen, said MR device collecting said MR data from said specimen at a plurality of different diffusion gradient durations, diffusion gradient strengths and diffusion gradient directions, whereby different ones of said plurality of diffusion times indicate the time-dependence of diffusion, and a computer, wherein said MRI device is communicably connected to said computer, said computer for executing the pulse sequence, and a computer, wherein said MRI device is communicably connected to said computer, for analysing said diffusion data collected by said MR device and applying said diffusion data to a Fourier transform, wherein the diffusion propagator is reconstructed, and a computer wherein said MRI device is communicably connected to said computer, for analysing said diffusion data collected by said MR device and applying said diffusion data to compute measures of dispersity.

FIG. 5: One embodiment of the proposed MR experiments. Three pulsed magnetic field gradients (depicted by grey boxes) are employed. q and q' are related to the gradient strength multiplied by the duration of the respective pulses.

FIG. 7: Contour plots showing a representative analysis. A contour plot of the signal plotted against q and q' is shown on the left. The technique described in the invention is applied on this data yielding an estimate of the propagator plotted against x and x' as shown in the centre. The analytical form of the propagator is used to generate the contour plot on the right.

FIG. 8: Surface plots representing the diffusion propagator estimated with increasing values of Δ (from left to right).

The invention claimed is:

1. A computer-implemented diffusion magnetic resonance method for determining a diffusion parameter for spin-labelled particles in a specimen, said method (100) comprising the steps of:
   providing (110) a specimen and a magnetic resonance device arranged to measure magnetic resonance in said specimen,
   applying (120), via at least one processor, at least one magnetic field gradient pulse sequence to said specimen, thereby spin-labelling a set of particles comprised in said specimen,
   obtaining (130), via the at least one processor, magnetic resonance measurement data corresponding to said at least one magnetic field gradient pulse sequence for said spin-labeled particles with said magnetic resonance device, wherein the obtaining (130) step comprises a diffusion-sensitized acquisition,
   determining (140), via the at least one processor, at least one diffusion parameter for said spin-labelled particles based on said obtained measurement data, and
   generating and displaying, via the at least one processor, at least one graphical representation of said determined at least one diffusion parameter for said spin-labelled particles,
   wherein:
      each magnetic field gradient pulse sequence comprises at least three gradient pulses, at least two of the at least three gradient pulses are configured to introduce phase shifts in said spin-labelled particles based on their position in said specimen at two different points in time, said at least two gradient pulses each having a duration shorter than one fourth of the sum of all gradient pulse durations of said magnetic field gradient pulse sequence, and
      said determining (140) step comprises forming, via the at least one processor and for each diffusion parameter, at least one Fourier transform, or numerical model fitting, representing said diffusion parameters based on said obtained measurement data and said at least two gradient pulses.

2. A magnetic resonance system for determining a diffusion parameter for spin-labelled particles, the system (300) comprising:
   a magnetic resonance device (340), and
   a computer (350) containing at least one processor configured to:
      control said magnetic resonance device (340) to project at least one sequence of magnetic field gradient pulses and radiofrequency pulses into a specimen (390) with the magnetic resonance device (340),
      collect magnetic resonance measurement data from said specimen (390) at a plurality of different gradient durations, gradient strengths and gradient directions with the magnetic resonance device (340), the collecting comprising a diffusion-sensitized acquisition,
      reconstruct at least one Fourier transform, or numerical model fitting, for each at least one diffusion parameter based on the collected magnetic resonance measurement data,
      determine the at least diffusion parameter based on the corresponding reconstructed at least one Fourier transform, or numerical model fitting, and
      generate and display at least one graphical representation of said determined at least one diffusion parameter,
   wherein:
      each gradient pulse sequence comprises at least three gradient pulses, at least two of the at least three gradient pulses are configured to introduce phase shifts in spin-labelled particles comprised in the specimen (390) based on position at two different points in time, said at least two gradient pulses each having a duration shorter than one fourth of the sum of all gradient pulse durations of said magnetic field gradient pulse sequence, and
      reconstructing said at least one Fourier transform, or numerical model fitting, for each of the at least one diffusion parameters is further based on said at least two gradient pulses.

3. The method according to claim 1, wherein the step of determining (140) at least one diffusion parameter comprises determining a diffusion propagator, a dispersity index, a local variance, a diffusion-weighted image, a steady-state distribution, a joint density distribution, and/or a set of cumulant tensors for said spin-labelled particles.

4. The method according to claim 1, wherein each gradient pulse sequence has an integral of gradient field strength over time for all gradient pulses that is substantially zero.

5. The method according to claim 1, wherein a plurality of gradient pulse sequences are applied, and wherein each gradient pulse sequence has a different gradient strengths, gradient directions, gradient durations, and/or delay times between gradient pulses, and wherein determining (140) the at least one diffusion parameter comprises forming the Fourier transform representing each diffusion parameter based on measurement data corresponding to said plurality of gradient pulse sequences.

6. The method according to claim 1, wherein obtaining (130) magnetic resonance measurement data comprises performing magnetic resonance spectroscopy, localized magnetic resonance spectroscopy, and/or magnetic resonance imaging with said provided magnetic resonance device.

7. The method according to claim 1, wherein determining (140) the at least one diffusion parameter comprises utilizing discrete Fourier transform, fast Fourier transform and/or analytical derivations.

8. The method according to any claim 1, wherein the step of determining (140) said at least one diffusion parameter comprises for each diffusion parameter forming a mathematical expression representing said diffusion parameter, wherein each mathematical expression comprises at least two Fourier transforms based on said obtained measurement data.

9. The method according to claim 1, said provided specimen comprising said spin-labelled particles is a porous media, soft-matter, food products, cultured or post mortem biological tissue, simulated materials, simulated tissue, synthetic materials, artificial tissue models, tissue slices and/or cell cultures.

10. The method according to claim 1, further comprising calibrating said magnetic resonance device based on the determined at least one diffusion parameter.

11. A computer program product comprising a non-transitory computer-readable storage medium (412) having thereon a computer program comprising program instructions, the computer program being loadable into a processor (411) and configured to cause the processor (411) to perform the method (100) of claim 1.

12. System according to claim 2, wherein the computer (350) is further configured to calibrate the magnetic resonance device based on diffusion measurements.

13. System according to claim 2, wherein said magnetic resonance device is configured to obtain measurement data utilizing magnetic resonance spectroscopy, localized magnetic resonance spectroscopy, and/or magnetic resonance imaging.

* * * * *